United States Patent
Taylor et al.

(10) Patent No.: US 7,333,921 B2
(45) Date of Patent: Feb. 19, 2008

(54) SCALABLE, CONCURRENT, DISTRIBUTED SENSOR SYSTEM AND METHOD

(76) Inventors: Stephen Taylor, P.O. Box 976, Grantham, NH (US) 03753; Peter Haaland, 518 W. Linden St., Louisville, CO (US) 80027-3124

( * ) Notice: Subject to any disclaimer, the term of this patent is extended or adjusted under 35 U.S.C. 154(b) by 0 days.

(21) Appl. No.: 11/382,340

(22) Filed: May 9, 2006

(65) Prior Publication Data

US 2007/0265796 A1 Nov. 15, 2007

(51) Int. Cl.
G06F 17/40 (2006.01)
G06F 19/00 (2006.01)

(52) U.S. Cl. .............. 702/187; 340/500; 340/870.01; 702/1; 702/127; 702/188; 707/10; 709/201

(58) Field of Classification Search ........... 340/500, 340/540, 573.1, 573.2, 573.6, 577, 601, 679, 340/870.01, 870.02, 870.03; 702/1, 2, 3, 702/4, 127, 182, 183, 184, 185, 187, 188; 707/1, 10, 100, 102, 104.1; 709/201, 217, 709/218, 219, 251, 252
See application file for complete search history.

(56) References Cited

U.S. PATENT DOCUMENTS

| | | | |
|---|---|---|---|
| 3,754,215 A * | 8/1973 | Blomenkamp | 340/870.12 |
| 4,821,175 A | 4/1989 | Hikita et al. | |
| 5,280,612 A | 1/1994 | Lorie et al. | |
| 5,287,496 A | 2/1994 | Chen et al. | |
| 5,333,316 A | 7/1994 | Champagne et al. | |
| 5,546,580 A | 8/1996 | Seliger et al. | |
| 5,626,144 A * | 5/1997 | Tacklind et al. | 600/538 |
| 5,692,178 A | 11/1997 | Shaughnessy | |
| 5,758,149 A | 5/1998 | Bierma et al. | |
| 5,832,068 A * | 11/1998 | Smith | 379/114.14 |
| 5,946,083 A | 8/1999 | Melendez et al. | |
| 6,029,190 A | 2/2000 | Oliver | |
| 6,138,118 A | 10/2000 | Koppstein et al. | |
| 6,654,782 B1 | 11/2003 | O'Brien et al. | |
| 6,735,630 B1 | 5/2004 | Gelvin et al. | |
| 6,754,656 B1 | 6/2004 | Cornwell et al. | |
| 6,762,684 B1 * | 7/2004 | Camhi | 340/573.1 |

(Continued)

FOREIGN PATENT DOCUMENTS

EP 1 093 288 A2 * 4/2001

(Continued)

*Primary Examiner*—Edward R Cosimano
(74) *Attorney, Agent, or Firm*—Christie, Parker & Hale, LLP.

(57) ABSTRACT

A sensor system and method for collecting and analyzing sensor data transmitted by various distributed sensors in a secure, scalable, and efficient manner. Sensors having sensor data to transmit establish concurrent connections with a central server that is configured to collect the sensor data. For each connection, the server generates a single writer thread dedicated to the connection. Each single writer thread accesses the server's underlying file system and writes the sensor data into a sensor file dedicated to the sensor. Each sensor file is written by a single writer thread, but may be concurrently read by multiple reader threads. Analysis threads may also concurrently access the sensor files to perform complex analyses of the stored sensor data. The analysis results are written to dedicated analysis files. The analysis threads act as single writer threads in writing to the analysis files.

27 Claims, 7 Drawing Sheets

U.S. PATENT DOCUMENTS

| | | |
|---|---|---|
| 6,772,363 B2 | 8/2004 | Pedone et al. |
| 6,792,432 B1 | 9/2004 | Kodavalla et al. |
| 6,798,531 B1 * | 9/2004 | Paz-Pujalt et al. .......... 358/1.15 |
| 6,816,862 B2 | 11/2004 | Mulgund et al. |
| 6,898,590 B1 * | 5/2005 | Streifer ........................... 707/2 |
| 6,943,682 B1 | 9/2005 | Dowens et al. |
| 6,950,725 B2 | 9/2005 | von Kannewurff et al. |
| 6,989,751 B2 * | 1/2006 | Richards .................. 340/572.4 |
| 7,002,477 B1 * | 2/2006 | Camhi ...................... 340/573.1 |
| 7,123,141 B2 * | 10/2006 | Contestabile .......... 340/539.13 |
| 2002/0186818 A1 * | 12/2002 | Arnaud et al. ............... 378/165 |
| 2004/0085576 A1 * | 5/2004 | Paz-Pujalt et al. .......... 358/1.15 |
| 2004/0215523 A1 * | 10/2004 | Wulff et al. .................. 705/26 |
| 2005/0040944 A1 * | 2/2005 | Contestabile .......... 340/539.13 |
| 2005/0046583 A1 * | 3/2005 | Richards ................. 340/825.49 |
| 2005/0086526 A1 * | 4/2005 | Aguirre ....................... 713/201 |
| 2005/0224577 A1 * | 10/2005 | Rozenblat et al. ........... 235/385 |
| 2006/0029200 A1 * | 2/2006 | Tasker et al. ................ 379/126 |
| 2006/0243347 A1 * | 11/2006 | Humphrey .................... 141/95 |
| 2007/0027630 A1 * | 2/2007 | Sanchez ....................... 702/19 |
| 2007/0121626 A1 * | 5/2007 | Shepard ...................... 370/389 |

FOREIGN PATENT DOCUMENTS

| | | |
|---|---|---|
| EP | 1 304 862 A1 * | 4/2003 |
| EP | 0 926 608 B1 | 3/2004 |

* cited by examiner

SCALABLE, CONCURRENT, DISTRIBUTED SENSOR SYSTEM AND METHOD

FIELD OF THE INVENTION

This invention relates generally to acquisition, archiving, and analyzing sensor data, and more specifically, acquiring, archiving, and analyzing sensor data via a network of distributed sensors and servers in a manner that is secure, scalable, and computationally efficient.

BACKGROUND OF THE INVENTION

Existing distributed database architectures take a very general view of the organization of data, namely, that the principal operations on the data are queries that allow multiple clients to concurrently access, search, and update data, typically without complex computations. In order to facilitate this general view of data, databases provide complex and expensive serialization techniques to ensure that when multiple clients read and write respectively from and to the same data, the correct results are delivered. For example, the prior art teaches various complex locking mechanisms on the data to avoid intervening, conflicting updates and to achieve serialization. These locking mechanisms allow multiple clients to concurrently write to a particular item in a database, but require overhead elements that reduce access speed and increase computational complexity. Further, the architectures provide no explicit separation of data attributes to ensure that sensitive personal data are compartmentalized and isolated in the network architecture. The impact of these attributes becomes more severe as the size of the database and the frequency of accesses to the data increase. Prior art serialization techniques, therefore, suffer problems with scalability, security, and concurrency.

Existing mechanisms for mitigating the impacts of serialization such as logical control of query queues, prioritization, and nesting database structures still leave a lot to be desired in terms of scalability, security, and concurrency.

In addition to distributed database architectures, a variety of distributed sensor architectures also exist in the prior art. These sensor architectures generally fall into two groups. The first group focuses on application specific architectures that use off-the-shelf database technology for information storage and retrieval. The overhead elements in off-the-shelf database technology that are necessary to ensure atomicity reduce scalability, security, and concurrency as described previously.

The second group includes ad-hoc and self-organizing sensor networks that are concerned with management, communication, and synchronization among and between sensors. These architectures introduce new complexities concerned with distributed management of data and suffer from the same fundamental limitations of atomicity, serialization, and concurrency control. Further, there are many practical applications of distributed sensors that do not require sensors to communicate or interact with one another. For these applications the additional costs of organizing distributed sensor management, communication and synchronization are unwarranted and limit concurrency and scaling to large networks.

Thus, the problem with former distributed sensor architectures is that they add unnecessary computational overhead to the acquisition, archiving, and analysis of data provided by the networked sensors. The magnitude of this overhead increases dramatically as the number of sensors increases. In other words, prior art methods for integrating sensor networks are serialized and therefore poorly scalable. Another problem inherent in prior art sensor networks is a lack of security for the information that is delivered by sensors to the server.

Accordingly, a system and a method are desired for acquiring, archiving, and analyzing sensor data via a network of distributed sensors and servers that avoids complex mechanisms for serialization, atomicity, locking protocols, and concurrency control and that inherently protects sensitive data.

SUMMARY OF THE INVENTION

According to one embodiment, the present invention is directed to a distributed sensor system that includes a plurality of sensors capable of concurrently collecting and transmitting sensor data. Each sensor is uniquely identified by a sensor identifier. The system further includes a server configured to concurrently connect to each of the plurality of sensors and generate a single writer thread dedicated to each connection. Each single writer thread automatically accesses a file system and writes sensor data transmitted by a corresponding one of the plurality of sensors into a sensor file dedicated to the corresponding sensor. The sensor file is identified by a sensor identifier of the corresponding sensor.

According to one embodiment of the invention, the server is further configured to generate an analysis thread responsive to an analysis trigger. The analysis thread accesses the file system for retrieving sensor data from one or more sensor files, analyzes the retrieved sensor data, and writes analysis results into an analysis file maintained by the file system. The analysis file may be identified by a sensor identifier of the analyzed sensor file, or by a code associated with a set of analyzed sensor files.

According to one embodiment of the invention, the server is further configured with multiple reader threads. These may be generated for handling concurrent access of the contents of one or more sensor files identified by the corresponding sensor identifiers. Each sensor file is therefore written by a single writer thread, but may be concurrently read by multiple reader threads.

According to one embodiment of the invention, the system further includes a data store storing private data associated with the sensor data. Examples of private data include the identity of individuals that are using sensors, the geographic location of sensors, and other details whose disclosure compromises the security of the networked sensors. The data store is physically separate from the server storing the sensor data.

According to one embodiment of the invention, the private data correlates a sensor identifier of the sensor collecting sensor data with private identifying information (e.g. name, social security number, address) about the particular individual that is being sensed.

According to one embodiment of the invention, the private data for a particular individual includes correlation of an analysis file identifier of an analysis file containing analysis data associated with the particular individual. According to this embodiment the private data may include correlations among a set of sensors or analysis file identifiers and a set of individuals.

According to another embodiment, the present invention is directed to a server coupled to a plurality of sensors in a distributed sensor system. The server includes a data store storing a plurality of sensor files under control of a file system.

According to one embodiment of the invention, the server also includes a connection manager thread configured to concurrently establish a connection to each of the plurality of sensors and generate for each connection a single writer thread dedicated to the connection. The single writer thread automatically accesses the file system and writes sensor data transmitted by the corresponding sensor into one of the plurality of sensor files, the one of the plurality of sensor files being dedicated to the corresponding sensor.

According to one embodiment of the invention, the server further includes an analysis thread generated responsive to an analysis trigger. The analysis thread accesses the file system for retrieving sensor data from one or more sensor files, analyzes the retrieved sensor data, and writes analysis results into an analysis file maintained by the file system.

According to one embodiment of the invention, a connection is established between the server and one or more analysis terminals. The connection manager thread according to this embodiment is configured to generate, for each connection with one of the analysis terminals, a reader thread for reading sensor data in a particular sensor file identified by the corresponding analysis terminal.

According to one embodiment of the invention, the connection manager is further configured to generate for each connection with one of the analysis terminals a reader thread for reading analysis data in a particular analysis file identified by the corresponding analysis terminal.

According to another embodiment, the present invention is directed to a method for collecting and analyzing sensor data in a distributed sensor system. The method includes establishing concurrent connections between a server and a plurality of sensors in the distributed sensor system; generating a single writer thread dedicated to each connection; and automatically writing into a sensor file dedicated to the corresponding sensor via the single writer thread, sensor data transmitted by a corresponding one of the plurality of sensors.

It should be appreciated, therefore, that the system and method according to the embodiments of the present invention allow sensor data transmitted by various distributed sensors to be analyzed in a secure, scalable, and efficient manner without resorting to complex mechanisms for serialization, atomicity, locking protocols, and concurrency control.

These and other features, aspects and advantages of the present invention will be more fully understood when considered with respect to the following detailed description, appended claims, and accompanying drawings. Of course, the actual scope of the invention is defined by the appended claims.

DETAILED DESCRIPTION

In general terms, embodiments of the present invention are directed to an architecture that integrates networked sensors with high-performance servers in a manner that is secure, intrinsically scalable, and computationally efficient for collecting, archiving, analyzing, and disseminating measurement information. The architecture enables high-performance, computationally intensive analytical models and archival storage from multiple sensors that are operated, maintained, and protected in a central location. This is unlike prior art architectures that use database systems that require complex mechanisms for serialization, atomicity, locking protocols, and concurrency. Instead of a database system, embodiments of the present invention use single writer threads that write the sensor data to an underlying file system directly, enhancing concurrency while eliminating the overhead and scaling limitations of databases.

According to one embodiment, a thread is a single sequential locus of control comprising a piece of software running on a computer. According to this embodiment, a thread is characterized by the state of the registers in the computer including the program counter that specifies how much of the software has been executed at a specific time. A person of skill in the art should recognize, however, that a thread is not limited to this definition, but may include all other definitions that will be apparent to a person of skill in the art.

According to one embodiment of the invention, the following organizational concepts help eliminate the problems of existing distributed sensor architectures:

1. A sensor is a unique source of data.
2. Each sensor transmits its data through an independent connection to a data communications network.
3. A sensor does not modify data that have been transmitted.
4. Each stored data file has one writer but may have multiple readers.
5. Neither data nor communications are shared among sensors.
6. Private data associated with a sensor (e.g. name, address, social security number of a medical patient using the sensor), and sensor data collected from the sensor (e.g. blood pressure and heartbeat measurements) are physically separated.

Throughout FIGS. 1-5, threads of execution are denoted in as ellipses, computers and sensors are shown as rectangles, connections are shown as lines, and data files are shown schematically as cylinders.

Figure 1:
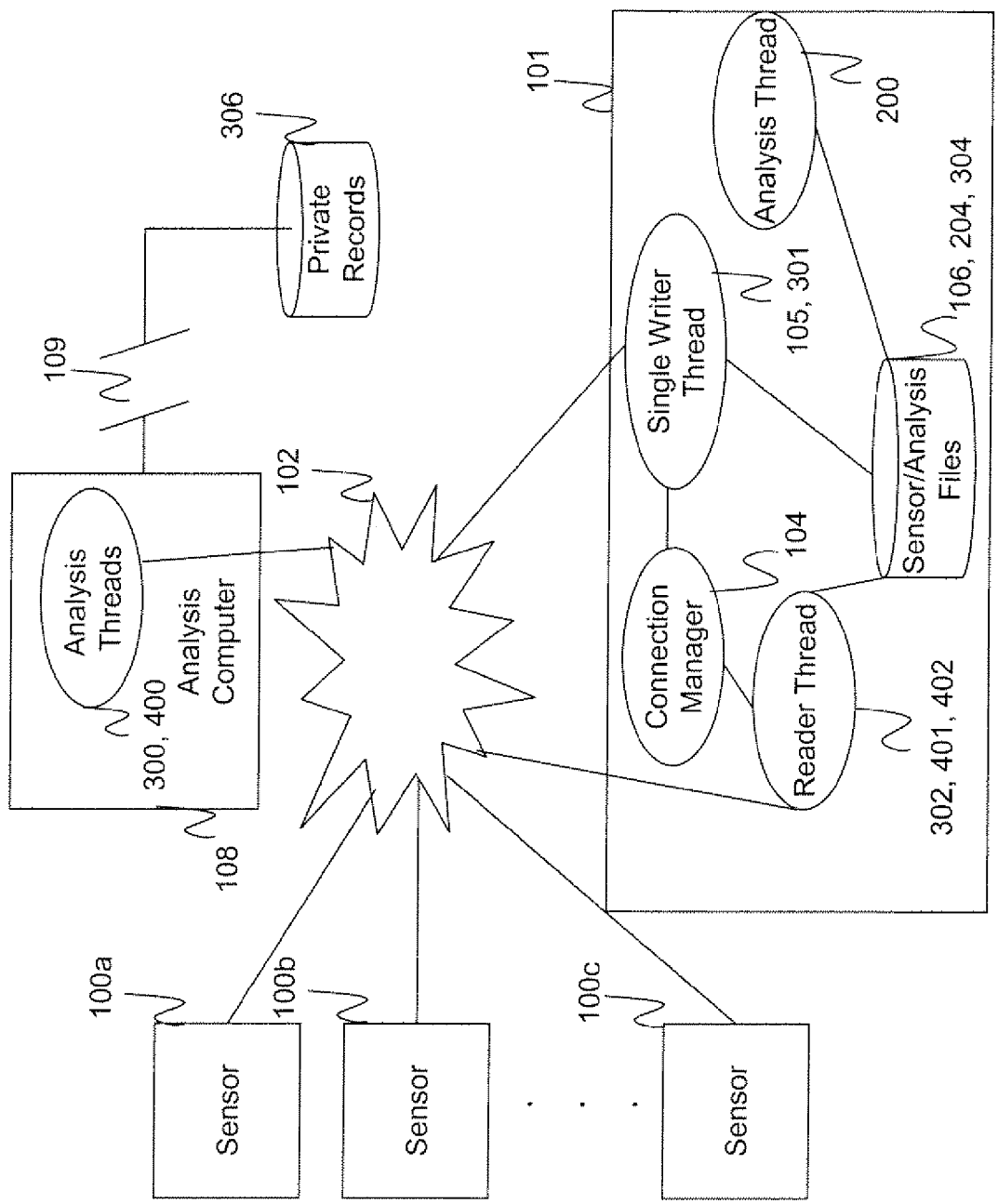
FIG. 1 is a schematic block diagram of a distributed sensor system according to one embodiment of the invention.

FIG. 1 is a schematic block diagram of a distributed sensor architecture according to one embodiment of the invention. The system includes one or more sensors 100a-100c (collectively referenced as 100) coupled to a server or cluster of servers 101 over a data communications network 102. The data communications network may be, for example, a local area network, private wide area network, the public Internet, or the like, which is implemented over a telephone exchange, fiber optic network, or other networking technologies using independently wired or wireless connections conventional in the art.

Figure 2:
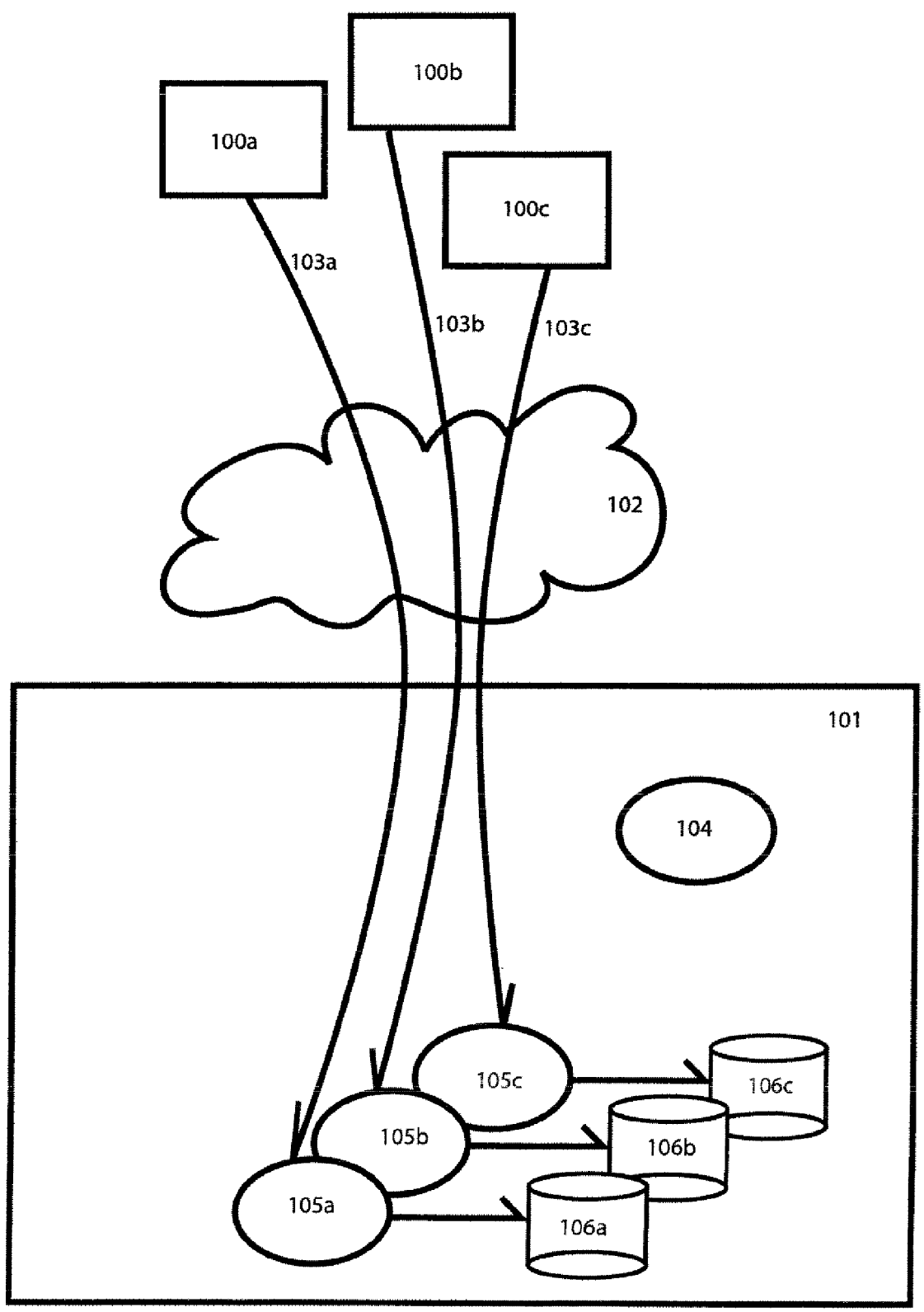
FIG. 2 is a block diagram illustrating sensor data collection in the distributed sensor system of FIG. 1 according to one embodiment of the invention.

Referring to FIG. 2, each sensor 100 is a device capable of obtaining, sensing, monitoring, and/or measuring different types of signals or inputs. For example, in a medical sensor network scenario, the sensor may be an electronic glucose monitor for diabetic patients, an electronic spirometer for asthmatic patients, an electronic scale for obese patients, a blood-pressure monitor for cardiac patients, and the like. A person of skill in the art should recognize, however, that the present invention is not limited to medical sensors, and may extend to other sensors capable of obtaining sensor data.

According to one embodiment of the invention, each sensor 100 is uniquely identified by a sensor identifier (ID) which may take the form of a serial number, code, or other identifying mechanism known in the art. If the sensor is intended to be used by more than one individual, the sensor ID includes one or more subfields in the sensor ID that is used to distinguish one individual from another. However, the subfields do not contain any personal data that may be used to reveal the individual's identity. All data that are stored, read, and/or subsequently processed from a sensor 100 are then associated only with its sensor ID.

The server 101 is a high-performance, shared-memory multi-processor having the ability to generate concurrent processing threads which may be operated on any available processor. In this regard, the server 101 includes a connection manager thread 104 that intercepts a connection to and from the server 101, and generates an appropriate processing thread based on the connection that is formed. The connection manager may be implemented as a software module stored in memory and executed by a processor in the server. The connection manager may also be implemented via hardware, firmware, or a combination of hardware, firmware, and/or software.

According to one embodiment of the invention, three types of processing threads in addition to the connection manager thread are supported by the current architecture: single writer threads, analysis threads, and reader threads. Single writer threads 105 allow the sensors 100 to directly access an underlying file system and concurrently write sensor data into a file 106 dedicated to each sensor with no requirement of synchronization, serialization, locking, or concurrency control. The file 106 is stored in a data store that may take the form of any mass storage device conventional in the art.

Figure 3:
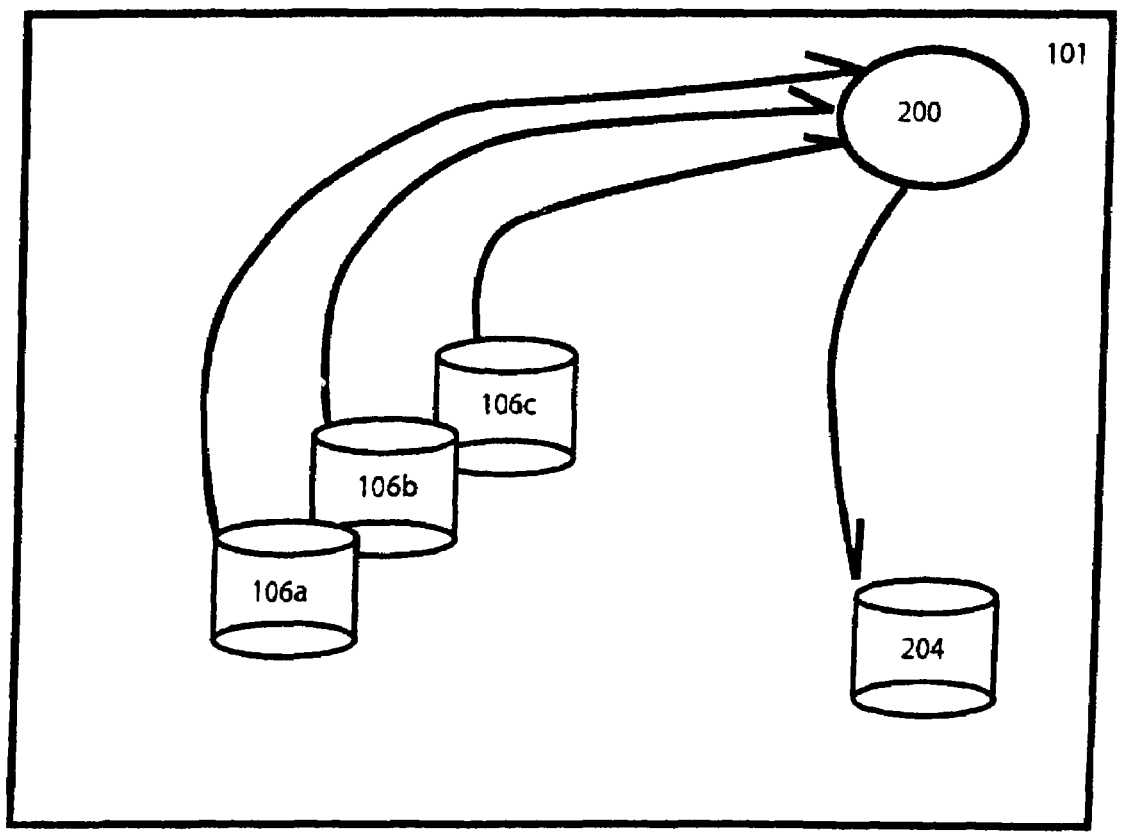
FIG. 3 is a block diagram illustrating sensor data analysis in the distributed sensor system of FIG. 1 according to one embodiment of the invention.

Analysis threads 200 are generated at the server 101 if the server is configured to do the analysis as described further with respect to FIG. 3. Alternatively, analysis threads 300, 400 may be executed at one or more analysis computers 108 as described further with respect to FIGS. 4 and 5. According to one example, the analysis threads may perform mathematical manipulations of sensor data to identify spatio-temporal patterns, anomalies, and the like. Each analysis thread may act as, or invoke, a single writer thread 301 for writing analysis data into a unique analysis file. The analysis file 204, 304 is also stored in the data store under control of the file system.

Reader threads 302, 401, 402 interface with analysis threads 300, 400 to concurrently access the file system and read sensor data stored in the sensor files 106 and/or analysis results stored in analysis files 204, 304. Reader threads also interface with one or more analysis threads executed in a remote analysis computer 108 for accessing sensor data requested by the analysis threads.

According to one embodiment of the invention, the remote analysis computers 108 have access to a data store 306 that stores private data of the individuals from whom sensor data are obtained. Such private data may include, for example, the individual's name, address, and/or social security number. Preferably, the private data are stored in a place that is physically separate from the sensor data. This separation, shown as 109 in FIG. 1, may be assured by an air gap, electronic firewall, encryption protocols, or other isolation methods familiar to those practiced in the art of computer security. The separation 109 of the private data helps ensure that only authorized analysts at the analysis terminals 108 can make an association between the private data and the corresponding sensor and/or analysis data. Thus, even in the event of a cyber attack on the sensors, servers, or associated connections, the private data are not compromised and cannot be related to information stored throughout the architecture.

FIG. 2 is a block diagram illustrating sensor data collection in the distributed sensor system of FIG. 1 according to one embodiment of the invention. Each sensor 100a-100c (collectively referenced as 100) that is ready to transmit sensor data establishes a connection 103a-103b (collectively referenced as 103) with the server 101. The connection manager 104 intercepts the connections and generates, for each connection, a single writer thread 105a-105c (collectively referenced as 105) that is dedicated to writing sensor data transmitted via the connection 103. According to one embodiment of the invention, the connection manager 104 generates the single writer thread 105, constructs a direct communication path between the thread and the sensor 100, and immediately terminates its involvement in the connection.

Each single writer thread 105 has access to the underlying file system that maintains unique sensor files 106a-106c (collectively referenced as 106) generated by the single writer threads. According to one embodiment of the invention, each single writer thread 105 is configured to receive all data emanating from the corresponding sensor 100 and store the data in the corresponding sensor file 106. According to one embodiment of the invention, each sensor file is identified by the sensor ID associated with the sensor that creates the connection 103. If a single sensor is used to collect sensor data for multiple individuals, the sensor ID includes a subfield that distinguishes the uses of the sensor by the different individuals, and hence, the sensor files for the different individuals are also distinguished.

The connection to the sensor is closed only after all data have been written to the corresponding file 106, ensuring serialization of write requests that emanate from the same sensor. Since the data associated with each sensor is appended to a unique and independent file, atomicity and synchronization across sensors are accomplished implicitly. Also, neither databases nor locking nor concurrency control protocols are used or needed in recording the sensor data.

FIG. 3 is a block diagram illustrating sensor data analysis at the central server 101 in the distributed sensor system of FIG. 1 according to one embodiment of the invention. Analysis may be triggered by a periodic trigger or an external event. An exemplary periodic trigger is a prediction of the onset of a catastrophic event such as, for example, an emergency room visit. This type of analysis may be performed once a month for low risk cases, but once a week or every other day for high risk cases. According to one embodiment of the invention, periodic analysis is scheduled programmatically at the server 101.

An exemplary external trigger is a request for analysis from a remote physician analyst, a request from a patient analyst for an update on their health, or collaborative exploration of data between multiple physician and patient analysts, via the analysis terminals 108. Because the analysts have access to the private data in the data store 306, the requests may be specific to an individual or a group of individuals, such as, for example, all patients between 30 and 60 years of age.

In the embodiment illustrated in FIG. 3, the analysis is performed locally by the server 101 via one or more analysis threads 200. Alternatively, the analysis may be performed by a remote analysis thread 300, 400 remotely at the analysis computer 108 as described with respect to FIGS. 4 and 5.

Each analysis thread 200 handles an analysis triggered by a particular trigger. For example, a monthly wellness check may be performed by one analysis thread to analyze all patient sensor files and generate a list of those patients that are in need of urgent attention. At the same time, a patient specific analysis may be performed by another analysis thread to verify a physician's treatment program or check for compliance with medication dosage and frequency. In this regard, each analysis thread reads one or more sensor files 106 in the underlying file system and analyzes the read sensor data. According to one embodiment of the invention, the read operations are non-blocking read operations which allow analysis to be performed up to and including the last complete data transfer from a sensor.

The analysis performed by a particular analysis thread 200 may be of an individual sensor file associated with a single sensor, or of multiple files corresponding to sets of sensors. The analysis results are stored in an analysis file 204 identified by an analysis file identifier. According to one embodiment of the invention, if the analysis concerns a single sensor file, the analysis file identifier is the unique sensor ID of the sensor file from which the analysis is derived. Alternatively, if analysis is concerned with multiple sensors, the analysis file identifier is a code that identifies the sensor set. This organization ensures that analysis threads are the single writers of all analysis files 204. Since analysis threads only consume data from sensor files, and do not write or modify a sensor file, serialization, locking, atomicity, and concurrency control are not required.

Once generated, the analysis file identified by the analysis file identifier is stored in the data store 204 under control of the file system. According to one embodiment of the invention, private data records of the individuals whose sensor data was analyzed are updated to identify the analysis file and/or time of the analysis. The analysis file identifier is retrieved and transmitted to the server 101 when requesting the analysis results stored in the particular analysis file. A separate analysis record may also be maintained at the analysis terminal 108 for maintaining track of analysis generated for particular individuals, individual groups, and the like.

Figure 4:
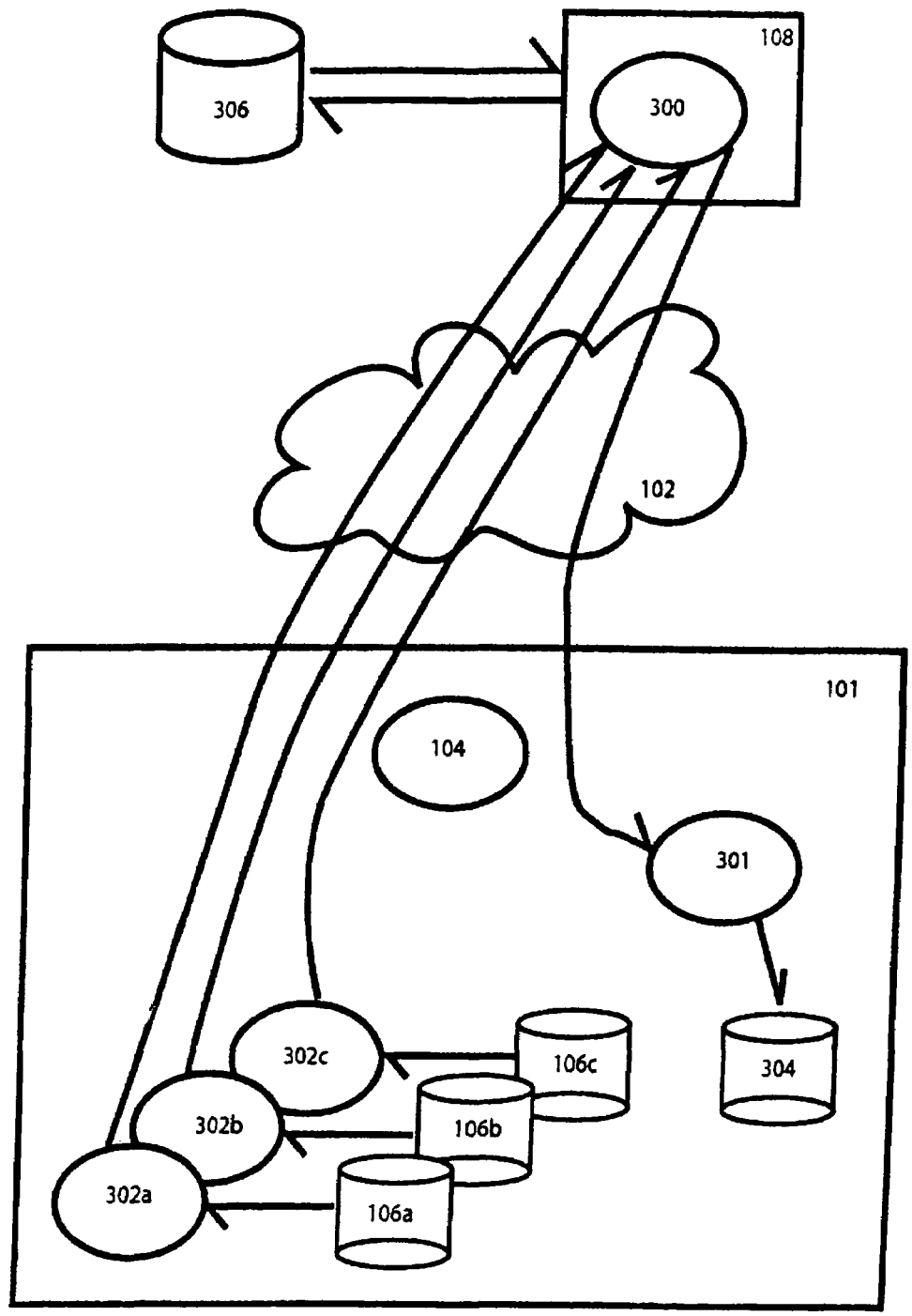
FIG. 4 is a block diagram illustrating remote sensor data analysis in the distributed sensor system of FIG. 1 according to one embodiment of the invention.

FIG. 4 is a block diagram illustrating remote sensor data analysis in the distributed sensor system of FIG. 1 according to one embodiment of the invention. According to this embodiment, analysis threads 300 are executed by the analysis computer 108 remotely from the server 101. The analysis threads may also be executed by the analysis terminals 108 according to alternate embodiments. According to the remote analysis embodiment of FIG. 4, one or more reader threads 302a-302c (collectively referenced as 302) and a single writer thread 301 interface with each analysis thread for communicating data to and from the analysis thread in the remote analysis computer 108. In this regard, the analysis data in the sensor files 106 is read by the reader threads 302 generated by the connection manager 104 upon receipt of an analysis request from the remote analysis thread 300. The read sensor data are then transmitted over the data communications network 102 for analysis by the remote analysis thread 300. Without loss of generality, this structure may be optimized for known sets of sensors to reduce the number of independent threads and connections by allowing reader threads to access multiple files and share connections.

The remote analysis thread 300 receives the sensor data and performs the analysis of the received data. The analysis results are transmitted back to the server 101, and the connection manager 104 generates the single writer thread 301 for the transmitted results. The single writer thread 301 writes the analysis results in a corresponding analysis file 304.

Figure 5:
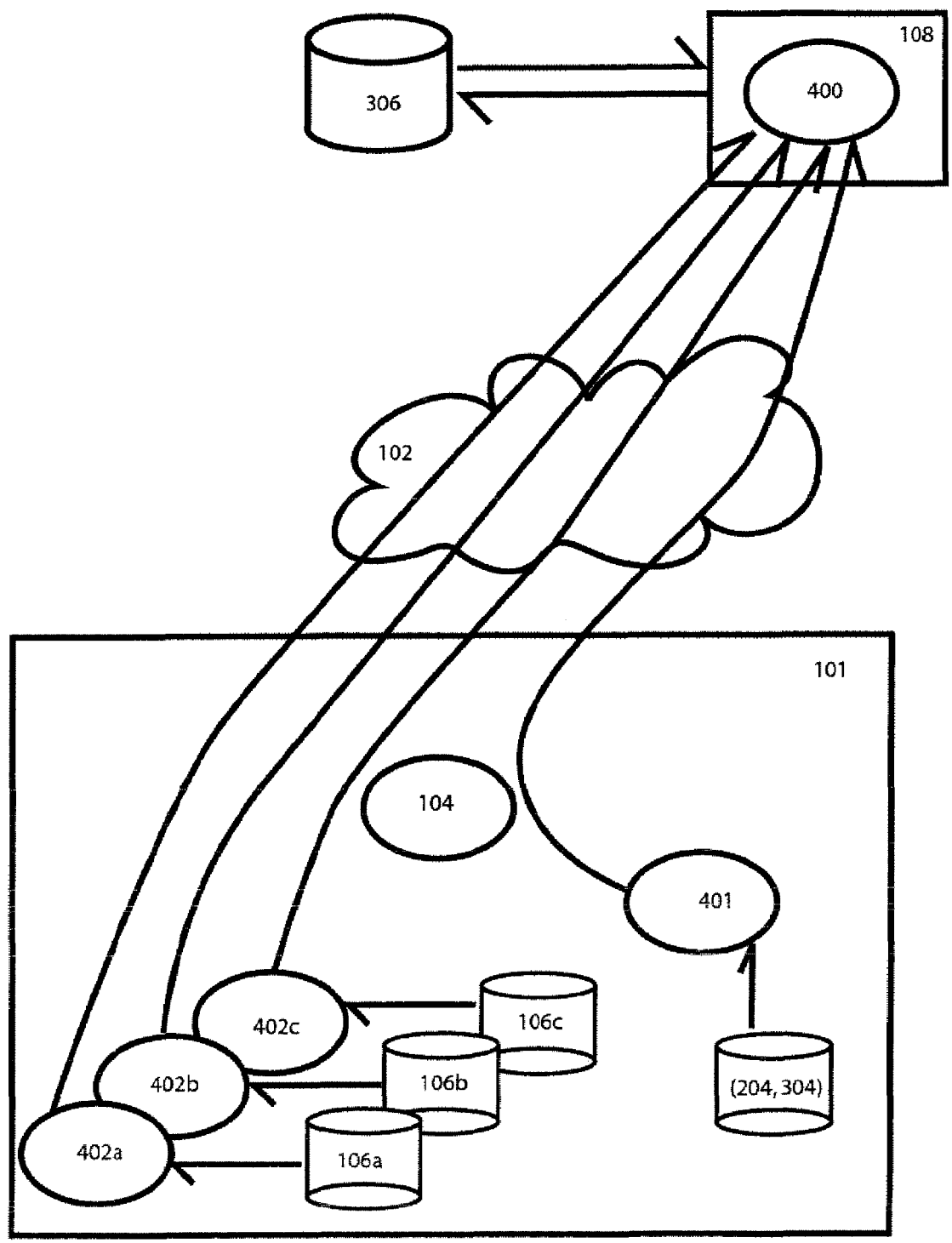
FIG. 5 is a block diagram illustrating access to sensor and/or analysis files by authorized users in the distributed sensor system of FIG. 1 according to one embodiment of the invention.

FIG. 5 is a block diagram illustrating access to sensor and/or analysis files by authorized users in the distributed sensor system of FIG. 1 according to one embodiment of the invention. Both sensor files 106 and analysis files 204, 304 may be concurrently accessed by authorized users having access to the analysis terminals 108 without constraining concurrency. All such accesses are read operations and may operate without synchronization to updates associated with the sensors 100 or analysis threads 200, 300.

Each analysis terminal 108 executes an analysis thread 400 for accessing and displaying data retrieved from the server 101. The analysis thread 400 is executed to allow authorized users to retrieve private data from the data store 306 and identify sensor files 106 or analysis files 204, 304 that they would like to retrieve, and transmit read requests to the server 101. One or more reader threads 401, 402a-402c (collectively referenced as 402) interface with a remote reader or analysis thread 400 for communicating data to the analysis thread. In this regard, the connection manager 104 generates the reader thread 402 for each requested sensor file 106, and the reader thread 401 for each requested analysis file 204, 304. The reader threads 401, 402 may concurrently access the requested files and transmit the read data to the requesting analysis thread running in the analysis terminal 108.

Analysis computers 108 may store intermediate data locally or in the private data store 306 using either single writer threads or conventional database technology.

Figure 6:
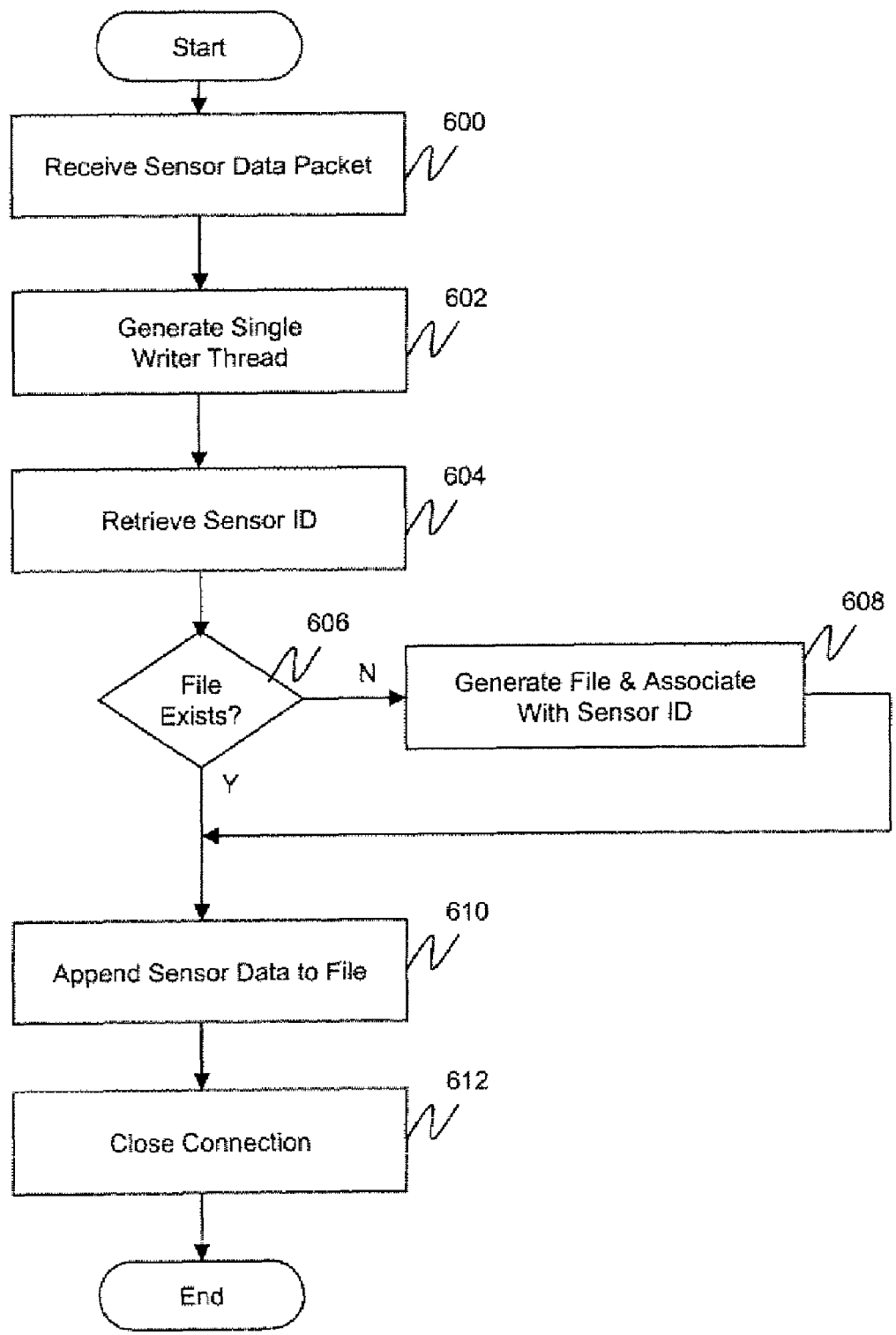
FIG. 6 is a flow diagram of a process for collecting sensor data from a particular sensor according to one embodiment of the invention.

FIG. 6 is a flow diagram of a process for collecting sensor data from a particular sensor 100 according to one embodiment of the invention. The process may be concurrently invoked for each sensor in the sensor architecture of FIG. 1 configured to concurrently transmit sensor data to the server 101.

Each sensor is initially setup by the individual from whom sensor data are obtained, or by another authorized individual (collectively referred to as authorized users). In this regard, the authorized user accesses the analysis terminal 108 to create or update a user record in the central data store 306 storing private data for the individual. The user record may be created or updated to store the individual's identification information such as, for example, user name, address, and social security number. The user record may further be created or updated to store the sensor ID of the sensor to be used to obtain sensor information from the individual. In a hospital setting where a particularly expensive sensor could be used for different patients, the sensor ID may include a subfield that distinguishes one individual's use of the sensor from another.

According to one embodiment of the invention, the authorized user may program the sensor to automatically obtain sensor data from the individual on a periodic basis. The sensor may be programmed directly by the authorized user, or remotely via the server 101. For example, a blood pressure sensor may be programmed to automatically measure the individual's blood pressure at set times. Of course, the sensor may also be manually operated to obtain sensor data from the individual whenever it is desired by the authorized user.

According to one embodiment, the authorized user may also program the sensor to automatically transmit the sensor data at periodic intervals. A transmission interval may be longer than the interval used in collecting the sensor data. For example, multiple measurements may be collected within a single collection interval, and the multiple measurements transmitted in a single communication session with the server 101.

Once the sensor has been setup, it proceeds to collect sensor data and engages in a handshake protocol with the server 101 for transmitting a sensor data packet with the collected sensor data to the server. According to one embodiment of the invention, the sensor data packet includes the acquired sensor data, a checksum, and the unique sensor ID. The transmitted data may be sent in the clear, or be encrypted via an encryption mechanism and/or include a digital signature as is conventional in the art.

in step 600, the connection manager 104 intercepts the connection with the sensor transmitting the sensor data packet and determines the validity of the received data based on the checksum information. If the data are deemed to be invalid, the sensor is requested to retransmit the data to the server 101. The server may keep track of multiple retransmissions associated with a sensor to infer when a sensor is becoming unreliable and in need of replacement. The handshake protocol may also incorporate periodic calibration of the sensor to ensure that it is functioning correctly and to verify its accuracy. This may be achieved, for example, upon the server uploading the calibration parameters to the sensor.

If the sensor data packet is valid, the connection manager 104 generates a single writer thread dedicated to the connection in step 602. In step 604, the single writer thread retrieves the sensor ID from the sensor data packet.

In step 606, the retrieved sensor ID is used to make a determination as to whether a file exists in the underlying file system for the transmitting sensor. If the answer is NO, the single writer thread proceeds to automatically generate, in step 608, a file dedicated to the sensor, and associates the retrieved sensor ID to the generated file. However, if a file matching the sensor ID already exists in the file system, the single writer thread simply opens the file.

In step 610, the single writer thread proceeds to record or append the received sensor data into the newly created or retrieved sensor file.

In step 612, after all the transmitted data has been written into the corresponding sensor file, the single writer thread proceeds to close the connection between the sensor and the server.

Figure 7:
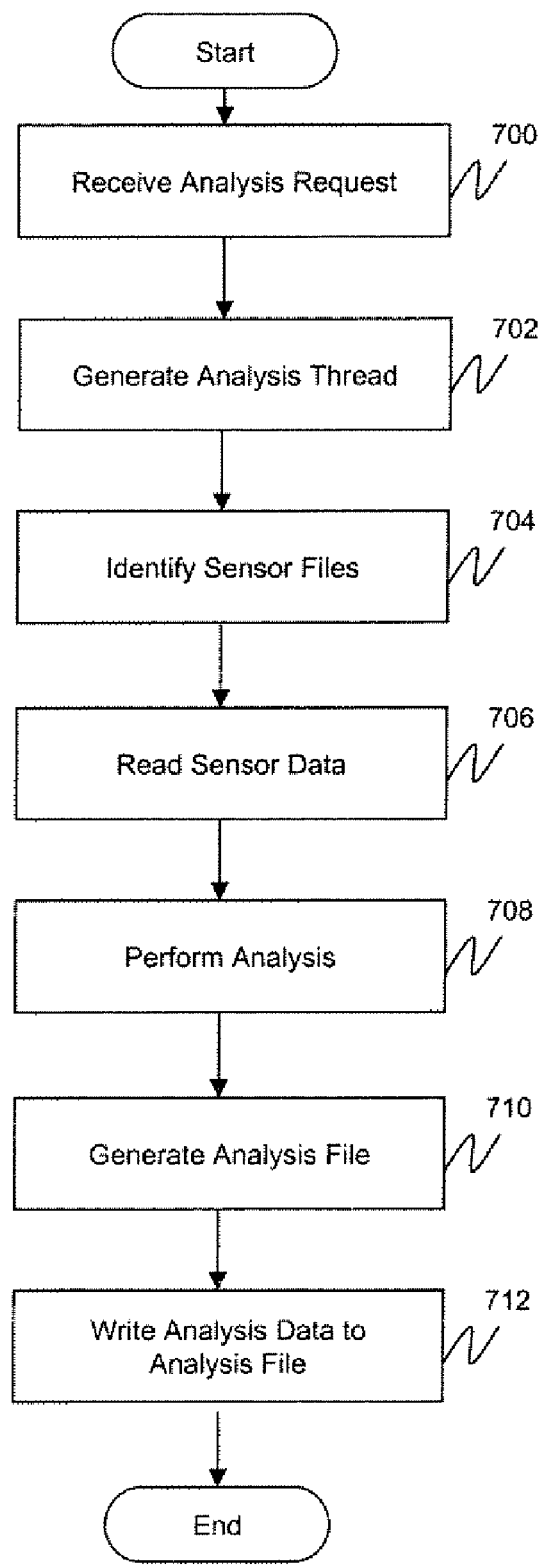
FIG. 7 is a flow diagram of a process for analyzing sensor data in response to an analysis request according to one embodiment of the invention.

FIG. 7 is a flow diagram of a process for analyzing sensor data in response to an analysis request according to one embodiment of the invention. The process may be concurrently invoked for each analysis thread that is concurrently invoked in response to an analysis trigger.

As discussed above, analysis may be triggered periodically or following a specific request from an authorized analyst. In either case, the analysis request may be specific to an individual or a group of individuals. Because the analysts know both the sensor ID of the sensor file containing an individuals sensor data as well as the individual's private data, the analysts may obtain from the server 101 the particular individual's sensor data and do the analysis locally, or request that the server 101 or separate analysis computer 108 perform the analysis and obtain only the results over the network connection. The latter are preferred when analysis requiring large data sets and data flows are too complex to be performed locally at the analysis site. An example of this includes an authorized analysis 400 being requested by a cellular telephone or a personal digital assistant.

If the analysis is to be performed by the server 101 or separate analysis computer 108, the analysis terminal 108 generates an analysis request in response to a particular analysis trigger, and transmits the request to the server or analysis computer.

In step 700, the server or analysis computer receives the analysis request, and in step 702, generates an analysis thread 200, 300 for handling the particular analysis request. According to one embodiment of the invention, the analysis request includes one or more sensor IDs of one or more sensor files to be analyzed by the analysis thread.

In step 704, the analysis thread identifies the appropriate sensor file(s) based on the sensor ID(s) included in the analysis request. In step 706, the analysis thread reads the sensor data in the identifies sensor file(s). If the analysis thread is executed by the analysis computer at a location remote from the server 101, the server 101 generates one or more reader threads for reading the sensor data in the identified sensor file(s), and transmitting the sensor data to the analysis computer.

In step 708, the analysis thread performs the requested analysis of the sensor data, and in step 710, generates an analysis file associated with the analysis. The analysis file is identified by the sensor ID of the sensor file used to perform the analysis if a single sensor file was analyzed, or a code that identifies a sensor set if multiple sensor files were analyzed. The generation of the code for the sensor set may be manual or automatic.

In step 712, the analysis results are written or appended to the analysis file using a single writer thread. The analysis results are also designated with a timestamp to disambiguate the results of a periodic analysis.

According to one embodiment of the invention, the analysis thread alerts the analyst that the requested analysis is complete. In its simplest form, the fact that analysis results are available upon request signify that the requested analysis is complete. Alternatively, the analysis terminals may be configured to periodically check and integrate the analysis results into a graphical display such as a table, graph, pie chart, or histogram. Generally, however, the analyst simply requests a most recent analysis for an individual or group of individuals, and the results of the analysis are displayed.

It should be appreciated that the architecture for sensor integration according to embodiments of the present invention enables unconstrained concurrency by ensuring that all data transfers are one-way. Neither serialization nor locking are required, and all access to data can be performed directly by the server operating system regardless of the number of active clients. Thus remote accesses can use both multi-threading and multi-processing without regard to the ordering of operations.

Embodiments of the present invention may be used for collecting, storing, and analyzing private medical information. The sensors 100 according to this usage are medical sensor devices. The sensor ID for each sensor 100 is linked to the patient's identity in a physically distinct record maintained by the medical caregiver at the central data store 306. Sensor data are written to sensor records 106 and read by the caregiver via the analysis terminals 108 or analysis computers 108. Sophisticated and computationally intensive analyses of the sensor data using techniques such as analysis of variance, Bayesian inference, nonlinear spectral analysis, and other techniques familiar to those skilled in the art of applied mathematics result in analysis records 204, 304 that are written by the caregiver and accessible over the data communications network 102 via reader threads 401. Because sensor files 106 are only written by sensors 100 via single writer threads 105 and analysis files 204, 304 are only written by analysis threads 200, 300, the method is intrinsically concurrent and scalable to very large sets of sensors, sensor files, and analysts. This is particularly useful for analysis of geographical and temporal epidemiology.

Embodiments of the present invention may also be used for polling individual opinions or perceptions. The sensor 100 according to this usage is a device that allows entry of survey responses such as, for example, a telephone, personal digital assistant, laptop, or desktop computer connected to the data communications network 102. The generated data files 106 are uniquely linked to the sensor ID of the input sensor. These files 106 are analyzed by statistical methods that may be computationally intensive and therefore benefit from the use of multi-threaded, shared-memory networked servers.

Embodiments of the present invention may further be used for automated security monitoring. The sensors 100 according to this usage acquire information about the environment such as, for example, acoustic signals, video or still images, chemical signals, electromagnetic signatures, and the like. The acquired sensor data are passed through the data communications network to the connection manager 104 and linked to corresponding sensor files 106 using single writer threads 105. The data are then read by analysis threads 200, 300 that evaluate baseline characteristics and generate alarms based on anomaly detection algorithms that may be computationally intensive.

Although this invention has been described in certain specific embodiments, those skilled in the art will have no difficulty devising variations to the described embodiment which in no way depart from the scope and spirit of the present invention. In addition, to those skilled in the various arts, the invention itself herein will suggest solutions to other tasks and adaptations for other applications. It is the Applicants' intention to cover by claims all such uses of the invention and those changes and modifications which could be made to the embodiments of the invention herein chosen for the purpose of disclosure without departing from the spirit and scope of the invention. Thus, the present embodiments of the invention should be considered in all respects as illustrative and not restrictive, the scope of the invention to be indicated by the appended claims and their equivalents rather than the foregoing description.

What is claimed is:

1. A distributed sensor system comprising:
   a plurality of sensors capable of concurrently collecting and transmitting sensor data;
   a server configured to concurrently connect to each of the plurality of sensors and generate, for each connection, a single-writer thread dedicated to the connection, each single-writer thread retrieving a sensor identifier unique to the sensor, automatically accessing a file system, and concurrently writing corresponding sensor data transmitted by the corresponding sensor into a corresponding sensor file uniquely identified by the corresponding sensor identifier without placing restrictions to prevent any other concurrently connecting sensor from writing any sensor data to the corresponding sensor file.

2. The system of claim 1, wherein the plurality of sensors are medical sensors, and the sensor data is medical sensor data.

3. The system of claim 1, wherein the server is further configured to:
   generate an analysis thread responsive to an analysis trigger, the analysis thread accessing the file system for retrieving sensor data from one or more sensor files, analyzing the retrieved sensor data, and writing analysis results using a single writer thread into an analysis file maintained by the file system.

4. The system of claim 3, wherein the analysis file is identified by a unique sensor identifier of the analyzed sensor file.

5. The system of claim 3, wherein the analysis file is identified by a unique code associated with a set of analyzed sensor files.

6. The system of claim 1 further comprising:
   a data store storing private data of individuals associated with the sensor data, the data store being physically separate from the server storing the sensor data.

7. The system of claim 6, wherein the private data for a particular individual includes the sensor identifier of the sensor collecting sensor data for the particular individual, the system further comprising:
   an analysis terminal coupled to the data store and the server, the analysis terminal transmitting a request for contents in a sensor file identified by the sensor identifier.

8. The system of claim 7, wherein the server is configured to generate multiple reader threads for handling concurrent access of the contents of the sensor files identified by the sensor identifiers.

9. The system of claim 6, wherein the private data for a particular individual includes an analysis file identifier of an analysis file containing analysis data associated with the particular individual, the system further comprising:
   an analysis terminal coupled to the data store and the server, the analysis terminal transmitting a request for contents in the analysis file identified by the analysis file identifier.

10. The system of claim 9, wherein the server is configured to generate multiple reader threads for handling concurrent access of the contents of the analysis file identified by the analysis file identifier.

11. A server coupled to a plurality of sensors in a distributed sensor system, the server comprising:
   a data store storing a plurality of sensor files under control of a file system;
   a connection manager configured to concurrently establish a connection to each of the plurality of sensors and generate, for each connections a single-writer thread dedicated to the connection, each single-writer thread retrieving a sensor identifier unique to the sensor, automatically accessing the file system, and concurrently writing corresponding sensor data transmitted by the corresponding sensor into a corresponding sensor file uniquely identified by the corresponding sensor identifier without placing restrictions to prevent any other concurrently connecting sensor from writing any sensor data to the corresponding sensor file.

12. The server of claim 11, wherein a connection is established between the server and one or more analysis terminals, the connection manager being further configured to generate for each connection with one of the analysis terminals a reader thread for reading sensor data in a particular sensor file identified by the corresponding analysis terminal.

13. The server of claim 11, wherein a connection is established between the server and one or more analysis terminals, the connection manager being further configured to generate for each connection with one of the analysis terminals a reader thread for reading analysis data in a particular analysis file identified by the corresponding analysis terminal.

14. The server of claim 11, wherein the plurality of sensors are medical sensors, and the sensor data is medical sensor data.

15. The server of claim 11 further comprising an analysis thread generated responsive to an analysis trigger, the analysis thread accessing the file system for retrieving sensor data from one or more sensor files, analyzing the retrieved sensor data, and writing analysis results into an analysis file maintained by the file system.

16. The server of claim 15, wherein the analysis file is identified by a sensor identifier of the analyzed sensor file.

17. The server of claim 15, wherein the analysis file is identified by a code associated with a set of analyzed sensor files.

18. A method for collecting and analyzing sensor data in a distributed sensor system, the method comprising:
    establishing concurrent connections between a server and a plurality of sensors in the distributed sensor system;
    generating, for each connection, a single-writer thread dedicated to the connection;
    each single-writer thread retrieving a sensor identifier unique to the sensor; and
    each single-writer thread automatically accessing a file system and concurrently writing corresponding sensor data transmitted by the corresponding sensor into a corresponding sensor file uniquely identified by the corresponding sensor identifier without placing restrictions to prevent any other concurrently connecting sensor from writing any sensor data to the corresponding sensor file.

19. The method of claim 18, wherein the plurality of sensors are medical sensors, and the sensor data is medical sensor data.

20. The method of claim 18 further comprising:
    generating an analysis thread responsive to an analysis trigger;
    accessing the file system via the analysis thread and retrieving sensor data from one or more sensor files;
    analyzing the retrieved sensor data via the analysis thread; and
    writing analysis results into an analysis file maintained by the file system.

21. The method of claim 20, wherein the analysis file is identified by a sensor identifier of the analyzed sensor file.

22. The method of claim 20, wherein the analysis file is identified by a code associated with a set of analyzed sensor files.

23. The method of claim 18 further comprising:
    storing private data of individuals associated with the sensor data in a data store that is physically separate from the server storing the sensor data.

24. The method of claim 23, wherein the private data for a particular individual includes the sensor identifier of the sensor collecting sensor data for the particular individual, the method further comprising:
    receiving from an analysis terminal a request for contents in a sensor file identified by the sensor identifier.

25. The method of claim 24 further comprising:
    generating multiple reader threads for handling concurrent access of the contents of the sensor file identified by the sensor identifier.

26. The method of claim 23, wherein the private data for a particular individual includes an analysis file identifier of an analysis file containing analysis data associated with the particular individual, the method further comprising:
    receiving from an analysis terminal a request for contents in the analysis file identified by the analysis file identifier.

27. The method of claim 26 further comprising:
    generating multiple reader threads for handling concurrent access of the contents of the analysis file identified by the analysis file identifier.

* * * * *